United States Patent [19]

César

[11] Patent Number: 4,484,343
[45] Date of Patent: Nov. 20, 1984

[54] TILTING TABLE X-RAY APPARATUS
[75] Inventor: Jean César, Nimes, France
[73] Assignee: National Equipment RX, Vitry-sur-Seine, France
[21] Appl. No.: 355,611
[22] Filed: Mar. 8, 1982
[30] Foreign Application Priority Data
Mar. 17, 1981 [FR] France ............... 81 05275
[51] Int. Cl.³ ............................ G03B 41/16
[52] U.S. Cl. .................... 378/196; 378/179
[58] Field of Search .......... 378/196, 179, 209, 197
[56] References Cited

U.S. PATENT DOCUMENTS

| 1,957,720 | 5/1934 | Nelson | 378/209 |
|---|---|---|---|
| 2,693,399 | 11/1954 | Vaughn | 311/6 |
| 3,068,357 | 12/1962 | Haupt | 378/179 |
| 3,086,115 | 4/1963 | Sutherland | 378/179 |
| 3,803,417 | 4/1974 | Kok | 250/447 |
| 3,838,287 | 9/1974 | Barrett | 378/196 |
| 3,967,126 | 6/1976 | Otto | 250/439 |

FOREIGN PATENT DOCUMENTS

| 214804 | 10/1909 | Fed. Rep. of Germany . |
|---|---|---|
| 1494016 | 7/1967 | France . |
| 2089965 | 12/1971 | France . |
| 2183387 | 11/1973 | France . |
| 657166 | 9/1951 | United Kingdom . |
| 745087 | 2/1956 | United Kingdom . |

Primary Examiner—Craig E. Church
Attorney, Agent, or Firm—Sandler & Greenblum

[57] ABSTRACT

A remote-controlled, tilting table X-ray apparatus comprises a patient-supporting table carried by a tilting frame. An X-ray examining assembly comprises an X-ray source spaced above the table. A film-holder selector is disposed beneath the table. A tilt axis for the frame on a stand is provided parallel to and on each side of a transverse axis of symmetry of the frame, the tilting mechanism tilts the frame with respect to the stand in either direction about a selected one of the tilt axes. A carriage supporting the X-ray source is movable mounted on a guide running longitudinally and outwardly of the frame. The X-ray examining assembly comprises ancillary member such as an image intensifier connected to the frame. The film-holder selector and the ancillary member are guided longitudinally of the frame.

6 Claims, 6 Drawing Figures

TILTING TABLE X-RAY APPARATUS

The present invention relates to a remote-controlled X-ray apparatus of the kind in which the X-ray pictures are taken beneath a tilting patient-supporting table which is carried by a frame movably mounted on a stand.

Various X-ray apparatus of this kind are known, which have, generally, the disadvantage of including relatively complicated and bulky mechanisms, such that they are not suitable for use by many potential users. Moreover, in known X-ray apparatus, the movable table, horizontal in its rest position, is generally at a considerable height above the ground, which presents certain disadvantages and is even a source of danger for some physically handicapped patients who have to climp on to the table and climb down after examination.

The undue weight of the table above the ground is particularly due to the size of the X-ray picture-taking means which must be situated beneath the table so that they can be brought to the selected portion of the patient's body somewhere along the length of the table. Bearing in mind the size of these X-ray picture-taking means, the manufacturers of tilting table X-ray apparatus are sometimes led to accept, to an undesirable extent, a compromise between the maximum possible inclination of the table and the height of the latter above the ground, in the horizontal position.

Such known X-ray apparatus often include a movable cantilever table, because their stand is shifted backwards away from the operator. The lack of rigidity due to such an arrangement tends to accentuate the effects of mechanical play in complicated tilting systems. These relatively expensive X-ray apparatus also have the disadvantage of poor quality X-ray pistures, particularly tomograms where there are simultaneous displacements of the X-ray source and of the sensitive film to be exposed. Finally, such known X-ray apparatus take a considerable amount of ground space. Similar remarks apply to X-ray apparatus with a pivot axis such as disclosed in French printed patent application No. 2,183,387.

An object of the invention is to provide a tilting table X-ray apparatus of the kind described above, which avoids the disadvantages of known X-ray apparatus and more particularly which takes up reduced floor space, has a low table in horizontal position, has a large tilting range, a considerable examination range, and is independent of the inclination of the table and very rugged, so as to ensure maximum convenience in use and to provide quality X-range pictures, particularly tomograms.

There is provided a remote-controlled, tilting table X-ray apparatus of the kind comprising a frame movably mounted with respect to a stand, a patient-supporting table carried by said frame, and X-ray examining assembly comprising an X-ray source and a support therefor spaced above said table and a film-holder selector disposed beneath said table, said X-ray apparatus being characterised in that a tilt axis for said frame is provided parallel to and on each side of a transverse axis of symmetry of said frame, and a tilting mechanism for tilting said frame with respect to said stand in either direction about a selected one of said tilt axes, a carriage supporting said X-ray source and said support therefor being movable mounted on a guide running longitudinally and outwardly of said frame, said X-ray examining assembly also comprising ancillary means connected to said frame, and means for guiding said film-holder selector and said ancillary means longitudinally of said frame.

Various parts of the tilting table arrangement are known per se but independently of one another. For example, the use of two parallel tilt axes for positioning some sort of mechanical member is disclosed in French patent No. 71 14075. The use of such tilt axes in the design of tables of X-ray apparatus is even contemplated in British patent No. 745,087, U.S. Pat. Nos. 2 693,399 and 3,068,357 but the X-ray source is then placed under the table.

Two tilt axes are also contemplated in French patent No. 1,494,016 but they are perpendicular to each other.

In other X-ray table in German patent No. 214,804 two parallel tilt axes are disclosed but the central part of the patient-supporting table between the tilt axes is stationary.

In yet another X-ray table disclosed in U.S. Pat. No. 3,967,126 the patient-supporting table does not tilt and the X-ray source is supported above the patient on a fixed column.

Finally in U.S. Pat. No. 3,803,417 there is disclosed an X-ray apparatus in which the X-ray source pivots around the patient but without being connected to a patient-support table which moreover is not tiltable.

As will be explained below, using two tilt axes one on each side of the transverse axis of symmetry of the frame as well as a sliding carriage outwardly of the frame makes it possible to provide a relatively compact stand therefor, well centered in relation to the table in its horizontal position, with the advantage of compactness and good rigidity of the linkage defined by the tilting mechanism installed in the stand. The compact arrangement of the stand allows maximum examination range, substantially over the entire length of the table, as explained in below.

Advantageously, the tilting table is mounted on a rectangular frame parallel to the table and articulated to the stand about its tilt axis; the X-ray examining assembly is mounted outwardly of the frame, for movement longitudinally along the frame, and bears a column which is substantially perpendicular to the frame and the table, in the normal position of this column; one end of the column carries a bracket for supporting the X-ray source facing the table, whereas the film-holder selector is supported and driven longitudinally of said frame.

With these characteristics it is possible to provide a tilting table X-ray apparatus which is convenient to use, as will be explained.

Preferably, the ancillary means project below the film-holder selector and away from said X-ray source, the stand comprising two vertical blocks of substantially the same height extending parallel to each other longitudinally of said frame and spaced transversely from each other so as to define a space for the passage of the ancillary means, X-ray examining the said means for guiding slidably mounting the ancillary means for displacement along the entire length of the table. The ancillary means may include a film charger cassette to one side of the film-carrier selector.

This special arrangement of the stand of the X-ray apparatus permits easy movement over the entire length of the table of the ancillary means mounted to project from the film-carrier selector, while at the same time the X-ray apparatus provides two tilt axes for the rectangular frame bearing the table relatively near the ground.

These and other characteristics and advantages of the invention will also emerge from the description of a preferred embodiment, given below by way of non-restrictive example, with reference to the attached drawings, in which.

Figure 6:
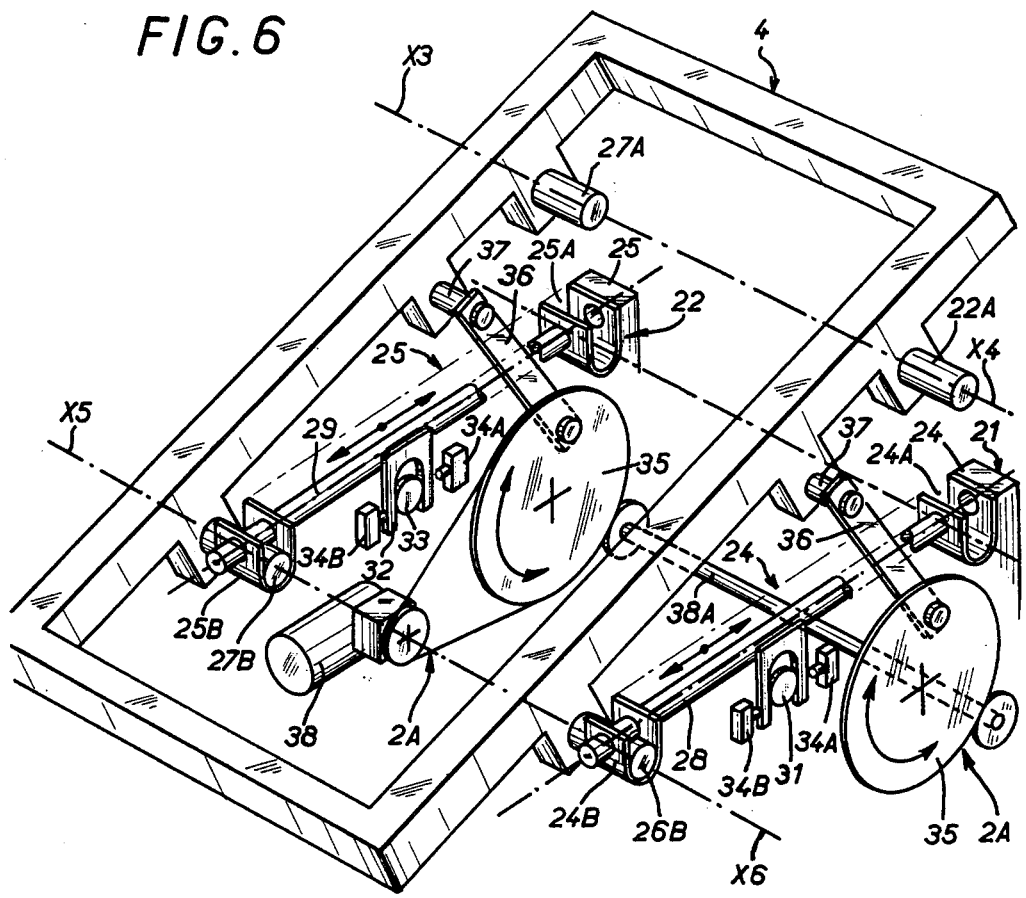
Figure 4:
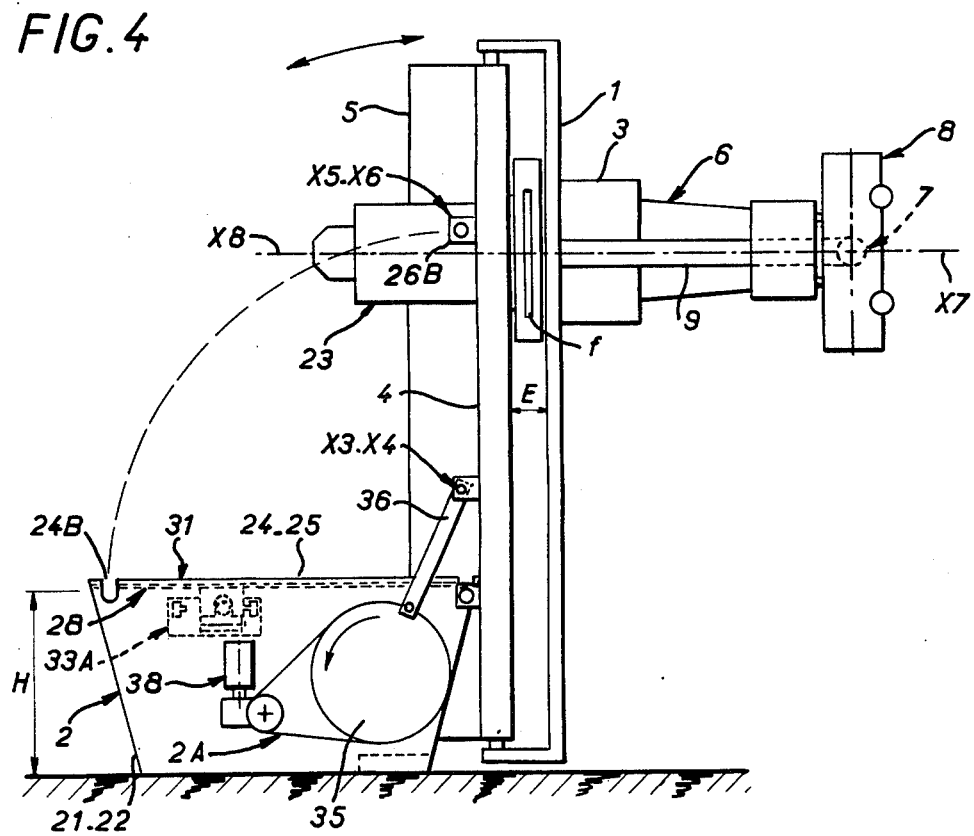
FIG. 4 is a front elevational view of the tilting table X-ray apparatus in the substantially vertical limit position of the table to one side of the stand, for picking up a patient standing on the floor with his back against the table.
Figure 5:
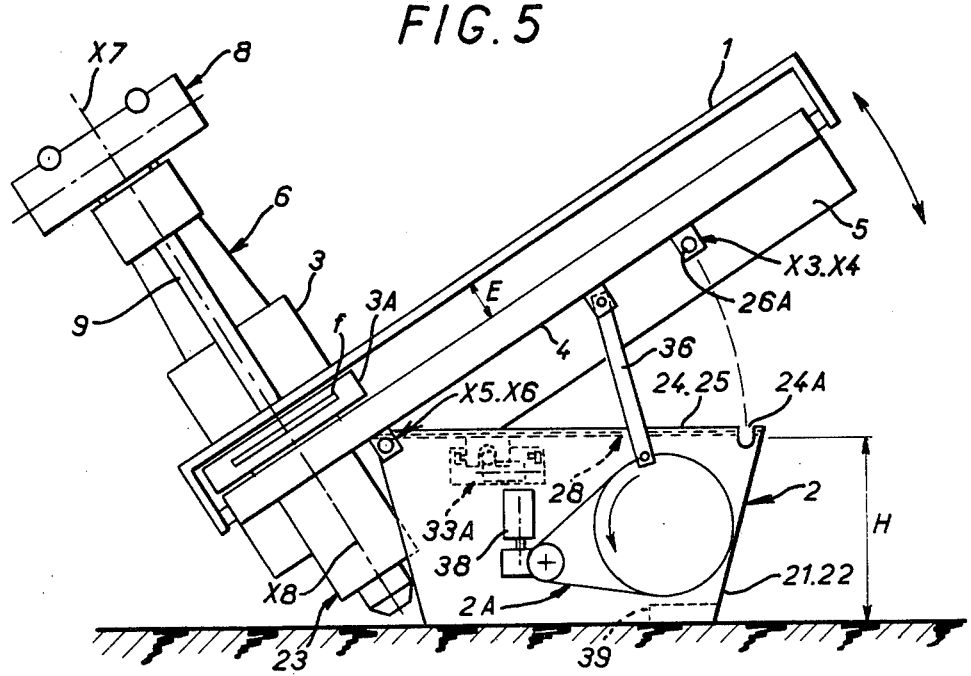

FIG. 5, similar to FIG. 4, shows the X-ray apparatus with the table tilted in the other direction so as to place the patient in the Trendelenburg examination position, lying on the table with his head down;

FIG. 6 is a diagrammatic perspective view of the tilting system for the intermediate or tilting frame with its four trunnions associated with retainer housings on the stand, the stand being provided with a tilting mechanism for controlling the tilting of the frame, and selective locking means for fixing each pair of trunnions in position in the corresponding pair of retainer housings.

In the embodiment of FIGS. 1 to 6, the X-ray apparatus has a substantially rectangular tilting table 1 which rests on a fixed stand 2, provided with a tilting mechanism 2A, described below for controlling the tilting movements of the table 1 (FIGS. 4 and 5). The table 1 is intended to accommodate a patient to be examined (not shown), and has for this purpose a longitudinally slidable carriage 3. The carriage supports X-ray examining means (described below) which can be brought to a selected part of the patient's body by displacement of the carriage.

The rectangular table 1 has on opposite sides of its transverse axis $X_1-X_2$ of symmetry two tilt axes $X_3-X_4$ and $X_5-X_6$, parallel to the short sides of a frame 4. The tilting mechanism 2A (described below) comprises means for tilting the table 1 relative to the stand 2, about a selected one of the tilt axes $X_3-X_4$ and $X_5-X_6$.

The tilting table 1 is mounted on the stand 2 and carried by the intermediate or tilting rectangular frame 4, which is parallel to the table 1 and articulated to the stand 20 about tilt axes $X_3-X_4$ and $X_5-X_6$. The sliding carriage 3 is mounted to one side and outwardly of the frame 4, on a slide 5 disposed along one of the long sides of the frame. A space "E" (FIGS. 1, 2, 4 and 5) is formed between the frame 4 and the table 1, to allow passage of spot-film means or a film-holder selector 3A, holding a X-ray or radiographic film, and fixed to the carriage 3. On the opposite side of the rectangular frame 4 of the carriage 3 bears a column 6, substantially perpendicular to the frame 4 and to the table 1, in the normal position of the column.

The upper end 6A of the column 6 carries a bracket 7 comprising an axis X12 at which is affixed an X-ray source 8 arranged facing the table, and the axis $X_7-X_8$ of the beam is centered on the spot-film means or film-holder selector 3A, disposed under the table 1. The association of the column 6 to the carriage 3 comprises a pivot axis $X_9-X_{10}$ parallel to the short sides of the rectangular platform 1, and means comprising, for example, a servo motor system or rocking mechanism 14 (described below) for rocking the column 6 to either side of its normal position, perpendicular to the table 1, coupling the movements of the column 6 with suitable displacements of the film-holder selector 3A or the frame 4 so as to obtain tomograms of the area of the patient's body which is being examined.

Means are provided for suitably coupling the rocking movements of the column 6 about its pivot axis $X_9-X_{10}$ and the longitudinal sliding movements of the film-holder selector 3A on the frame 4. For example, these means comprise a tomographic rod 9 one end of which is articulated about an axis X11 to the film-holder selector 3A, and the other end (FIG. 2) of which is rigidly fixed to the bracket 7 having an axis X-12 and bearing the X-ray source 8, so that the rod 9 will be strictly parallel to the axis $X_7-X_8$ of the beam from the X-ray source 8.

Figure 2:
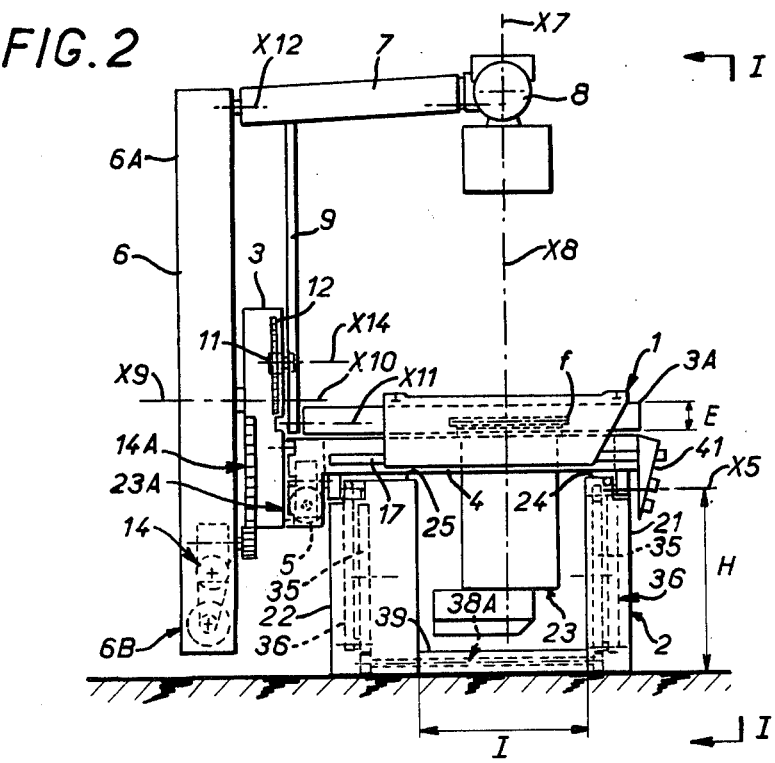
FIG. 2 is a side view of the table in FIG. 1, taken along the line II—II.

Axes X11 and X12 at the ends of the rod 8 are parallel to the pivot axis $X_9-X_{10}$ of the column 6, and the rod 9 moreover is joined to the carriage 3 by a third pivot axis X14, parallel to axes X11 and X12 and situated therebetween (FIG. 2).

The third pivot axis X14 of the rod 9 is defined by a connecting joint 11, having two portions pivoted to each other, one of which is fixed to the carriage 3 and movable vertically by a worm adjusting mechanism 12. The other portion of the connecting joint 11 is slidable along the rod 9. The practitioner or operator using the X-ray apparatus can also vary at will the homothetic ratio ensured by the rod 9, between the rocking movements of the bracket 7 bearing the X-ray source 8, about the axis X12, and the reciprocating displacements of the film-holder selector 3A, these displacements taking place when the column 6 is itself subjected to rocking movement about its pivot axis $X_9-X_{10}$, by means of the servo motor system or rocking mechanism 14 cooperating with a sector gear 14A on the lower portion of the carriage 3 (FIG. 2). The servo motor system or rocking mechanism 14 is mounted in the lower end 6B of the column 6 remote from the upper end 6A bearing the bracket 7 and the X-ray source 8, so as to counter-balance the column about the pivot axis $X_9-X_{10}$. As explained below this counter-balancing of the column 6 facilitates smooth rocking movements of the column, about its axis $X_9-X_{10}$ (FIG. 2) under the action of the rocking mechanism 14, avoiding jarring and vibration.

Figure 3:
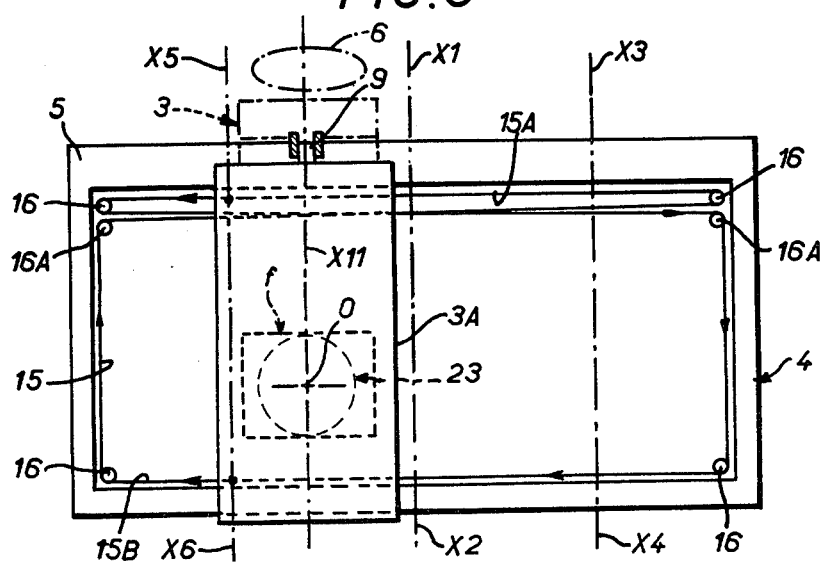
FIG. 3 is a diagrammatic plan view of a portion of the X-ray apparatus in FIG. 1, taken along line III—III showing the intermediate of tilting frame upon which the table rests, and the mounting of the film-holder selector on the carriage for sliding longitudinally of the rectangular frame.

When the column 6 swings or rocks in relation to the carriage 3, about its axis $X_9-X_{10}$, the tomographic rod 9 follows the movements of the bracket 7 connected to the top end 6A of the column, whilst remaining aligned with pivots axes X12, X14 and X11. These pivots axes X12, X14 and X11 are aligned with the column 6 only when the latter is in its its central position (FIG. 1), perpendicular to the plane of the table 1 and to the plane of the film f to be exposed, held in the film-holder selector 3A (FIGS. 2 and 3). For every inclined position of the column 6 in relation to the plane of the table 1, the position of the rod 9 is slightly more inclined, since the middle pivot axis X14 is nearer the pivot axis X12 of the bracket 7 than the pivot axis $X_9-X_{10}$ of the column. And the lower end of the rod 9, connected to the film-holder selector 3A at the pivot axis X11, transmits through the axis X11 of the film-holder selector 3A a longitudinal reciprocating movement. The magnitude of the rectilinear displacements of the film-holder selector 3A and the magnitude of the angular displacements of the pivot axis X12 in relation to the pivot axis X9–X10 of the column are related to each other according to a homothetic ratio which the operator can control at will by using the worm adjustment mechanism 12 which controls the distance of the pivot axis X14 of the connecting joint 11 (FIG. 2) from the pivot axis X9–X10 of the column.

In order to ensure precise guidance of the film-holder selector 3A between the frame 4 and the table 1 whilst keeping the film-holder selector constantly parallel to itself in its reciprocating movements controlled by the rod 9 supported by carriage 3, one end of the film-holder selector close to the lower end of the rod 9 is fixed to one stretch 15A of a conjugation cable 15 arranged in the plane of the rectangular frame 4, and reeving idle pulleys 16 fixed at the four corners of the rectangular frame 4 (FIG. 3). Another end of the film-holder selector 3A, opposite the rod 9 and supported by frame 4, is fixed to another stretch 15B of the cable 15. Stretches 15A and 15B are parallel and driven with precisely identical movements, by virtue of the crossing over of the stretches of the cable 15, running over the two intermediate pulleys 16A. Owing to this guidance of the opposite ends of the film-holder selector 3A, the latter always remains parallel to itself, the pivot axis X11 of the lower end of the rod 9 defining at all times the axis of symmetry of the film-holder selector 3A parallel to the transverse axis of symmetry X1–X2 of the frame 4. Along the axis of symmetry of the selector 3A there is situated the centre 0 of the area to be exposed on the film f held in the film-holder selector.

Thus there is ensured precise guidance of the film-holder selector 3A, by servo control of the reciprocating movements of the latter with the pivoting movements of the rod 9, whereby the axis X7–X8 of the X-ray beam (FIGS. 1 and 2) passes at all times through the centre 0 of the area to be exposed on the film f in the film-holder selector 3A.

As explained below, this makes it possible to obtain, selectively, excellent tomograms of the area of the patient's body situated substantially in a plane parallel to the film f, at the level of the pivot axis X14 of the rod. Indeed, the various points of this area are the only ones which maintain a fixed position in relation to the centre 0 of the tomogram to be taken, whereas the images of all the other parts of the patient's body reached by X-ray beam from the source 8 in relation to the other parts of the patient's body.

In order to facilitate, in the crosswise direction, a precise centering of the different parts of the rectangular table 1 in relation to the axis X7–X8 of the X-ray beam 8 (FIG. 2), the table 1 is slidably mounted on its support frame 4 by means of guides 17 parallel to the short sides of the rectangular table and the transverse axis of symmetry X1–X2.

By an appropriate selection of the height H of the stand 2, at the level of the tilt axes X3–X4 and X5–X6 of the frame 4 (FIGS. 1, 2, 4 and 5), as a function of the length of the frame 4 and the table 1 beyond the tilt axes, the tilting mechanism 2A makes it possible to bring the table 1 and the frame 4 to a substantially vertical position to the side of the strand 4 corresponding, for example, to the tilt axis X3–X4 (FIG. 4). The patient is then in the upright position, with his back against the table 1. In the other direction, to the side of the other tilt axis X5–X6, the tilting mechanism 2A allows considerable tilting of the table 1 upon which the patient is reclining, so as to place his head, in the Trendelenburg examination position, frequently used by practitioners for examining the abdominal region.

Figure 1:
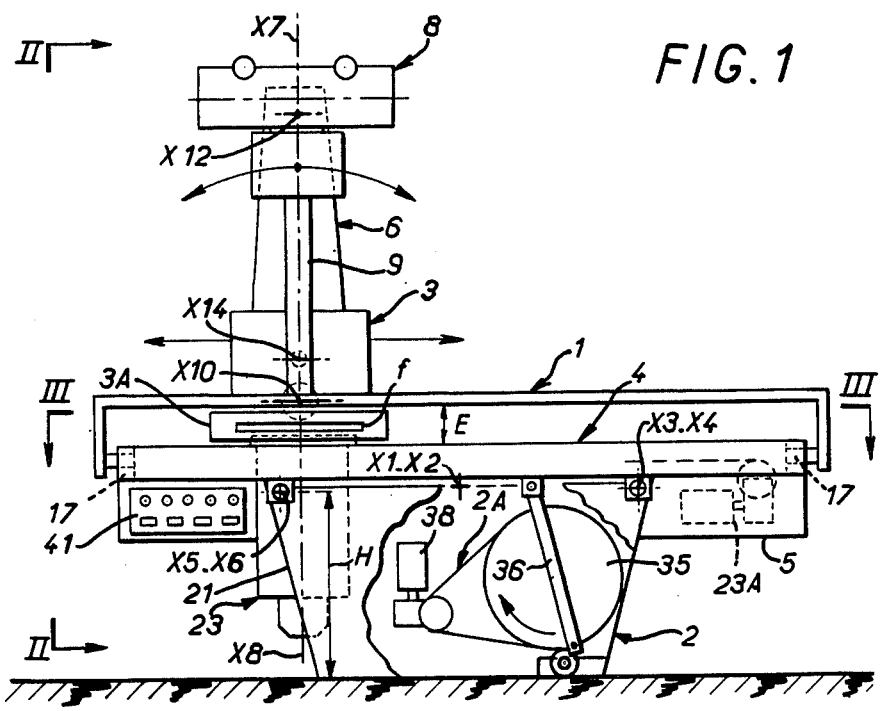
FIG. 1 is a front elevational view of a tilting table X-ray apparatus embodying the invention, in a horizontal position of the table.

The stand 2 comprises two parallel, longitudinally extending vertical blocks 21, 22 (FIG. 2) of substantially the same height. The blocks 21, 22 of the stand are spaced transversely of each other so as to define therebetween a space I to allow the passage of ancillary means 23 of the radiological examing means mounted to project below the film-holder selector 3A opposite the X-ray source 8. The ancillary means 23 thus accompany the film-holder selector A fixed to the carriage 3 over the entire length of the table 1, when the operator causes the displacement of the carriage 3 to bring the film-holder selector 3A relative to a part of the body of the patient to be examined. To do this, the operator activates a motor 23A fixed to the slide 5 (FIGS. 1 and 2). The ancillary means 23 may comprise an image intensifier which serves to improve the quality of the X-ray pictures and a film charger cassette to one side of the film-holder selector 3A.

Each of the vertical blocks 21, 22 of the stand 2 is situated substantially plumb with one of the longitudinal sides of the rectangular frame 4, and has, in relation to the associated longitudinal side, a substantially rectilinear and horizontal upper edge 24, 25 having at each end a retainer housing 24A, 24B, 25A, 25B (FIGS. 4, 5 and 6). Each retainer housing 24A, 24B, 25A, 25B is U-shaped and opens upwardly, and has a bight or bottom consisting of a substantially semi-cylindrical trough, with a horizontal axis, joining two vertical walls. The four retainer housings, 24A, 24B, 25A, 25B of the stand 2 are placed at the corners of a rectangle centered substantially symmetrically under the rectangular frame 4, in the horizontal position to the latter, and each retainer housing is designed to receive one of the horizontal trunnions 26A, 26B, 27A, and 27B of the frame 4, is axis coinciding with a tilt axis X3–X4, X5–X6. With each pair of trunnions 26A, 27A and 26B, 27B aligned along one of the tilt axes X3–X4 and X5–X6 there is associated a pair of retainer housings 24A, 25A and 24B, 25B.

In the horizontal position of the frame 4, the pairs of trunnions 26A, 27A and 26A, 27B are received in the corresponding pair of retainer housings 24A, 25A and 24B, 25B in order to support the frame 4 in a stable position (FIGS. 1 and 2). In the inclined position of the frame 4, about one of the tilt axes X3–X4 and X5–X6 (FIGS. 4 and 5), one of the pairs of trunnions 26A, 27A, and 26B, 27B will be received in the corresponding pair of retainer housings 24A, 25A or 24B, 25B. The other pair of trunnions is then free to tilt with the frame 4 relative to the stand 2. Stability of the frame 4 in the inclined position is ensured by connecting rods 36, described below, articulated to the under part of the frame and fixed to the tilting mechanism 2A arranged in the stand 2. Each retainer housing 24A, 24B and 25A, 25B of the stand 2 is connected to three-position locking means 28, 29 (described below) for selectively locking the two pairs of trunnions 26A, 27A and 26B, 27B, of the frame 4, in the two associated pairs of retainer housings in the stand 2 (FIG. 6). In the central position of the locking means, corresponding to the horizontal position of the frame 4 (FIGS. 1 and 2), both pairs of trunnions of the frame 4 are locked in the corresponding pairs of retainer housings of the stand 2. In either of the limit positions of the locking means 28, 29 corresponding to an inclined position of the frame 4 on the stand 2 (FIGS.

4 and 5), one pair of the trunnions 26A, 27A and 26B, 27B, is locked into the corresponding pair of retainer housings 24A, 25A or 24B, 25B of the stand 2.

In the preferred arrangement shown in FIG. 6, the locking means include in each block 21, 22, of the stand 2 a horizontal sliding rod 28, 29 having three positions, close to the upper edge 24, 25 of the corresponding block. Each sliding rod 28, 29 extends transversely to the horizontal axes of the semi-cylindrical troughs defining the bottoms of the retainer housings 24A, 24B and 25A, 25B provided at the ends of the upper edges 24, 25 of the stand 2. The length of each sliding rod 28, 29 is slightly greater than the distance between the horizontal axes of the corresponding two semi-cylindrical troughs. Each end of both the rods 28, 29 is selectively engageable in two holes which are provided in registration with each other in the vertical walls of each retainer housing 24A, 24B and 25A, 25B and passes over a trunnion 26A, 26B and 27A, 27B of the frame 4, the trunnion bearing on the bottom of the housing, so as to lock the rod into place. In its central position, each sliding rod 28, 29 thus locks the trunnions 26A, 26B and 27A, 27B in the two retainer housings 24A, 24B and 25A, 25B in the upper edges 24, 25 of the stand 2 (FIGS. 1 and 2). Each sliding rod 28, 29 in either of its limit positions (FIGS. 4, 5 and 6) locks a single trunnion 26A, 27A, or 26B, 27B into the corresponding retainer housing 24A, 25A, or 24B, 25B.

The two sliding, locking rods 28, 29 are actuated simultaneously in the arrangement illustrated in FIG. 6, each sliding, locking rod 28, 29 in the block 21, 22 of the stand 2 carries at its middle a substantially flat fork 31, 32 with two prongs extending transversely to the axis of the sliding rod 28, 29. An actuating disc 33, driven in rotation by a motor 33A (FIGS. 4 and 5) about an axis eccentric to the disc, is mounted between the two parallel prongs of each fork 31, 32. And means for simultaneously actuating said locking rods described below, are provided for ensuring for identical movements of the two eccentric fiscs 33 identical movements of the two sliding rods 28, 29 in order to cause the sliding rods to move simultaneously into each of their three positions. The means for simultaneously actuating said sliding rods 28, 29 comprise, for example, in each block 21, 22 two switches 34 A, 34B cooperating respectively with the parallel prongs of each fork 31, 32, which is secured to a sliding rod 28, 29 so as to determine each of the three positions of the sliding, locking rods, and to ensure pairing or coupling of the motors 33 A (FIGS. 4, 5) which drive in rotation the actuating discs 33 (FIG. 6).

The tilting mechanism 2A which serves to control the tilting movements of the rectangular frame 4 comprises, for example, in each block 21, 22 of the stand 2, a crank 35 with its axis parallel to the tilt axes X3–X4 and X5–X6 of the frame 4. Each crank 35 is attached to one of the ends of a connecting rod 36, the other end of each connecting rod is articulated to the under part of the frame along one of the long sides thereof, about a pivot 37 having an axis parallel to the tilt axes and arranged between these. The cranks 35 arranged in the two blocks 21, 22 of the stand 2 are identical, as are the connecting rods 36, and are designed to operate in an identical manner, driven by a motor 38 driving one of the cranks 35. The said one crank 35 is connected to the other crank 35 by a connecting shaft 38A parallel to the tilt axes X3–X4 and X5–X6 and extending between the blocks 21, 22 in the base 39 of the stand 2, constituting a bed plate between the blocks (FIG. 2).

We shall now describe the operation of the tilting table X-ray apparatus which has just been described with reference to FIGS. 1 to 6.

The control of the X-ray apparatus is effected by a control panel 41, disposed on a lateral face of the frame 4 (FIGS. 1 and 2) and having a certain number of push-buttons. These pust-buttons enable a practitioner or operator using the apparatus to control the various parts of the apparatus, and more particularly the motor 23A which displaces the carriage 3 longitudinally, the motor 38 for the tilting mechanism 2A which controls the tilting of the frame 4, and on the rocking mechanism 14 associated with the column 6.

Starting from the horizontal rest position of the tilting table, bearing at both ends against the stand 2 (FIG. 1) the practitioner obtains the desired inclination of the table 1 by pushing the appropriate button of the panel 41, to start the motor 38 of the tilting mechanism 2A (FIG. 6) so as to bring the table 1 into an inclined position between the limit positions of FIGS. 4 and 5. Then, by controlling the motor 23A for the carriage 3 (FIGS. 1 and 2) the operator adjusts, as required, the longitudinal position of the carriage 3, so as to bring the film-holder selector 3A and the X-ray source 8 into the desired position facing the area to be X-rayed in the body of the patent, lying on the table 1 or standing on the floor with his back against the table standing vertically upright (FIG. 4). If necessary, the operator adjusts the patient's body in relation to the centre 0 of the film f to be exposed in the film-holder selector 3A (FIG. 3), by acting upon the motor for transverse displacement (not shown), which ensures, parallel to the short sides of the rectangular table 1, tranverse sliding of the table on the transverse guides 17 of the frame 4 (FIG. 2).

Having thus ensured, in relation to the desired part of the patient's body, correct centering of the axis X7–X8 of the beam of the X-ray source 8, which coincides, by construction, with the centre 0 of the film f to be exposed, the operator can control the operation of the X-ray source 8, so as to produce an ordinary radiograph or X-ray picture of the particular area of the patient's body.

However, the operator can also control beforehand the rocking mechanism 14, situated at the lower end of the column 6 (FIG. 2) and, cooperating with the sector gear 14A at the lower end of the carriage 3, so as to impart rocking movement of the column 6 about its pivot axis X9–X10. As already pointed out, this rocking movement of the column 6 (FIG. 1) produces a linear movement of the film-holder selector 3A in the longitudinal direction of the table 1, under the action of the end of the tomographic rod 9 connected to the film-holder selector 3A through the pivot axis X11. At the same time the bracket 7 carrying the X-ray source 8 rotates about its horizontal axis X12, to ensure coincidence of the axis X7–X8 of the beam from the source 8 with the centre 0 of the film to be exposed (FIG. 3), under the action of the rod 9 parallel to axis X7–X8.

As indicated, the operator already chose a predetermined position of the pivot axis X14 of the rod 9, by adjusting this position by means of the adjustment worm 12, in relation to the plane of the table 1 against which the patient's body rests. The position of the axis X14 corresponds, in the patient's body, to an examination area substantially parallel to the film f and located at the level of the pivot axis X14 of the rod 9.

Owing to the movable mounting of the X-ray source 8, the axis X7–X8 of the X-ray beam coincides at all times with the centre 0 of the area of the film f to be exposed, one obtains an X-ray picture of particular clarity for all the points of the patient's body in the examination area, to the exclusion of points of the patient's body outside the area.

For use in the various conditions which have just been set forth, the tilting table X-ray apparatus has several important advantages compared with known apparatus.

Embodying the stand 2 in two parallel blocks 21, 22 with a space I therebetween (FIG. 2) makes it possible to have the table 1 at a relatively low height H above the floor, in the horizontal position, whilst facilitating over the entire length of the table displacements of the carriage 3 with the film-holder selector 3A beneath which there are affixed the ancillary means of the x-ray examining means 23, such as the relatively cumbersome image intensifier. This embodiment of the stand 2 moreover makes it possible to cause the table 1 to tilt vertically to one side of the stand (FIG. 4), whilst permitting in the other direction great tilting magnitude in the Trendelenburg position (FIG. 5) without having recourse to a complicated and onerous mechanisms for longitudinal displacement of the table 1, as in known X-ray apparatus.

The tilting mechanism for the intermediate frame 4 with the two pairs of trunnions 26A, 27A and 26B, 27B defining the two symmetrical tilt axes X3–X4 and X5–X6, ensures, in a simple way, great rigidity of the mobile unit defined by the frame 4 bearing the table 1, this unit bearing at the four points (FIG. 6) in all the positions of the table. This rigidity, particularly important for producing high quality tomograms, is improved by counter-balancing the column 6. The lower end 6B of the column contains parts by the rocking mechanism 14 which are heavy enough to provide a counterweight effect.

Owing to the absence of any real longitudinal displacement of the table 1, and the possibility of adjusting the position of the table 1 transversely, along the guides 17 of the frame 4 (FIG. 2), the patient can remain conveniently in the same position on the table 1, without having to move to achieve precision positioning. Meanwhile the operator uses the panel 41 (FIGS. 1 and 2) to control the motors which adjust the position of the table 1 and the carriage 3 in relation to the frame 4, so as to bring into registration the desired part of the patient's body, with the centre 0 of the film f to be exposed (FIG. 3), which coincides with the axis X7–X8 of the beam of the X-ray source 8 (FIGS. 1 and 2).

The embodiment of the tilting mechanism 2A comprising two connecting rods 36, articulated under the frame 4 and each connected to a crank 35 (FIG. 6) makes it possible to eliminate, advantageously, a variable-speed drive for the motor 38. In fact, the two limit positions of the table 1 (FIGS. 4 and 5) and the lower horizontal position of the table 1 (FIG. 1) correspond to a high or low dead-centre of the end of each connecting rod 36. For a given speed of rotation of the crank 35 the tilting frame 4 has an angular speed of arrival or departure which is equal to zero in each of the three positions which ensures in a simple way a smooth and shock-free operation of the tilting frame.

The selective locking means for pairs of trunnions 26A, 27A and 26B, 27B of the frame 4 consisting of the two sliding, locking rods 28, 29 driven by the eccentric discs 33 (FIG. 6) and controlled by the limit switches 34A, 34B is easy to be servo-controlled reliably with the positions of the tilting frame 4, controlled by the operator. For this purpose suitable circuits (not shown) connected particularly to the limit switches 34A, 34B for the sliding, locking rods 28, 29, and to the motor 38 for the tilting mechanism operation of the motor 38 if the sliding rods are not in the correct position.

A similar safety circuit controls the motor (not shown) which rotates the eccentric discs 33 for controlling the movements of the sliding, locking rods 28, 29 so as to prevent operation of this motor if the frame 4 is not precisely in the horizontal position, with its four trunnions engaged at the bottoms of the corresponding retainer housings in the stand 2.

Other safety circuits similarly prevent operation of the other motors of the table, particularly motor 23A which translates the carriage and the motor for the rocking mechanism 14 (FIGS. 1 and 2), if the locking system comprising the two rods 28, 29 is not in a position which will ensure correct locking of a pair of trunnions in an inclined position, ensuring the locking of both pairs of trunnions in the horizontal position. The operation of the X-ray source 8 controlled by the same safety circuits, which can easily be made to function automatically, precluding intervention by the operator, in all the positions of the tilting frame.

The invention is not of course restricted to the details of the embodiment which has been described by way of example. Various modifications and alternatives understood to those skilled in the art may be provided without departing from the scope of the invention. Thus, although there are described for the tilting mechanism of the table, a three position lock, one could envisage, a simpler embodiment with two positions.

What I claim is:

1. A remote-control tilting table x-ray apparatus which comprises:
    (a) a stand including two verticle blocks of substantially equal height which extend parallel to one another;
    (b) a frame movably mounted on said stand, said frame including two pairs of horizontal trunnions having axes which coincide with first and second tilt axes of said frame, said vertical blocks having upper edges with two pairs of retainer housings formed therein, said retainer housings comprising means for accommodating respective trunnions, said frame further comprising three-position sliding locking rods for selectively locking said trunnion pairs within respective pairs of retainer housings, said frame further comprising means for simultaneously actuating said locking rods;
    (c) a patient-supporting table carried by said frame;
    (d) an x-ray examining assembly comprising an x-ray source and a support therefor disposed above said table;
    (e) a film-holder selector disposed below said table;
    (f) first and second tilt axes for said frame, said first and second tilt axes being disposed parallel to and along each side of a transverse axis of symmetry of said frame;
    (g) means for tilting said frame with respect to said stand in either direction about either of said tilt axes;
    (h) a carriage for supporting said x-ray source and support, said carriage being movably mounted along a guide member which extends longitudinally and outwardly of said frame;

(i) ancillary imaging means being associated with said film-holder selector, said ancillary imaging means being connected to said frame and projecting below said film-holder projector and away from said x-ray source;

(j) means for guiding said film-holder selector and said ancillary imaging means longitudinally with respect to said frame, said ancillary imaging means being slidably mounted on said guiding means such that said ancillary imaging means can be displaced along the entire length of said table; and (k) an eccentrically rotatable actuating disk disposed between two prongs of a fork which is fixed to and which extends transversely from each of said locking rods, wherein said means for simultaneously actuating said locking rods ensures identical movement of said locking rods among their three positions for identical movement of said actuating disks.

2. A remote-control tilting table x-ray apparatus in accordance with claim 1 wherein said ancillary imaging means comprises an image intensifier for improving the quality of x-ray pictures taken by said x-ray source.

3. A remote-control tilting table x-ray apparatus in accordance with claim 1 wherein said ancillary imaging means comprises a film cassette attached to said film-holder selector.

4. Apparatus according to claim 1 wherein said means for guiding said film-holder selector comprises a conjugation cable, said film-holder selector being connected at an end adjacent said carriage to a stretch of said conjugation cable lying in a plane defined by said table, said conjugation cable being reeved over idle pulleys mounted at four corners of said frame, the end of said film-holder selector remote from said carriage being fixed to another stretch of said conjugation cable parallel to the first-mentioned stretch, said stretches of conjugation cable being connected together by a crossing over of two intermediate pulleys.

5. Apparatus according to claim 1, wherein said means for simultaneously actuating said locking rods comprises switches cooperating with the respective prongs of said forks.

6. Apparatus according to claim 1 wherein said tilting mechanism comprises identical cranks disposed inside said vertical blocks, each of said cranks having an axis parallel to said tilt axes of said frame and being connected to one end of a control rod, the other end of said control rods being pivotally connected to said frame about an axis parallel to said tilt axes, and motor means for driving one of said cranks, and a connecting shaft extending parallel to said tilt axes and connecting said cranks together for ensuring movement in unison.

* * * * *